(12) United States Patent
Raffel et al.

(10) Patent No.: US 6,422,992 B1
(45) Date of Patent: Jul. 23, 2002

(54) TOTAL BODY RELAXATION SYSTEM AND METHOD

(75) Inventors: Mark J. Raffel, Port Washington; Kenneth Seidl, Saukville; Gregory Elliott, Port Washington; David Vang, Adell, all of WI (US)

(73) Assignee: Raffel Product Development Co., Inc., Saukville, WI (US)

( * ) Notice: Subject to any disclaimer, the term of this patent is extended or adjusted under 35 U.S.C. 154(b) by 0 days.

(21) Appl. No.: 09/364,927

(22) Filed: Jul. 29, 1999

(51) Int. Cl.[7] .............................................. A61M 21/00
(52) U.S. Cl. ....................................................... 600/27
(58) Field of Search .............................. 600/27, 26, 28, 600/547; 434/236; 601/15; 128/897, 898

(56) References Cited

U.S. PATENT DOCUMENTS

| | | | |
|---|---|---|---|
| 2,684,670 A | 7/1954 | Mathison | |
| 4,173,217 A | 11/1979 | Johnston | 128/734 |
| 4,365,637 A | 12/1982 | Johnson | 128/734 |
| 4,625,732 A | 12/1986 | Kasa et al. | 128/670 |
| 4,966,158 A | 10/1990 | Honma et al. | 128/734 |
| 5,021,768 A | 6/1991 | Kishida et al. | 340/573 |
| 5,024,650 A * | 6/1991 | Hagiwara et al. | 600/26 |
| 5,266,070 A * | 11/1993 | Hagiwara et al. | 600/27 |
| 5,304,112 A * | 4/1994 | Mrklas et al. | 600/27 |
| 5,704,902 A | 1/1998 | Vandenbelt et al. | 601/72 |
| 5,807,287 A | 9/1998 | Cheng | 601/60 |
| 6,067,468 A * | 5/2000 | Korenman et al. | 600/547 |

* cited by examiner

*Primary Examiner*—Kevin Shaver
*Assistant Examiner*—Brian Szmal
(74) *Attorney, Agent, or Firm*—Michael Best & Friedrich LLP

(57) ABSTRACT

A total body relaxation system comprising a plurality of vibrating elements and a control circuit connected to the vibrating elements to provide an electrical stimulus to energize the vibrating elements, the control circuit including a stress sensing circuit for sensing relative total body stress and a display element for providing a visual indication of total body stress.

40 Claims, 3 Drawing Sheets

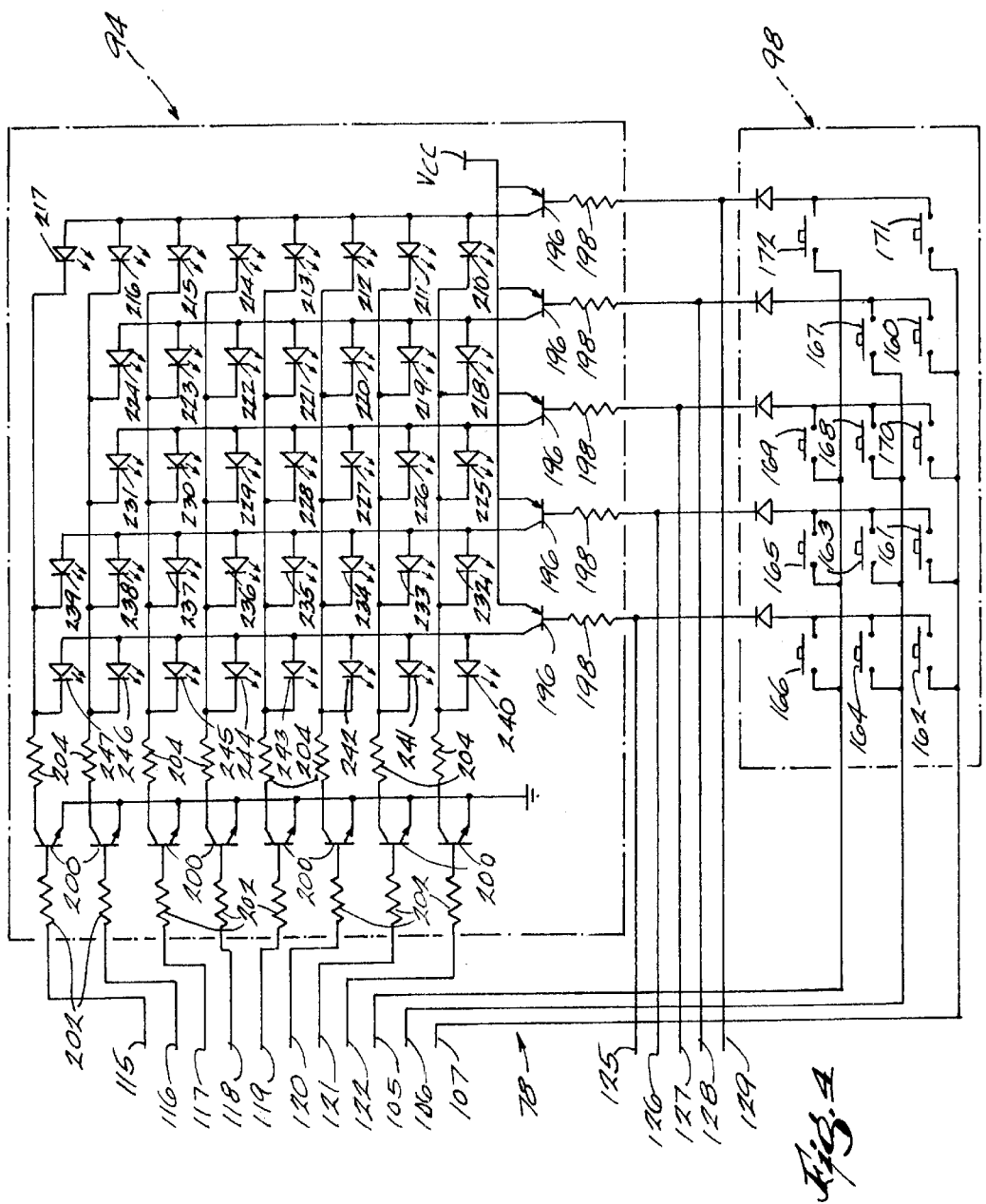

TOTAL BODY RELAXATION SYSTEM AND METHOD

BACKGROUND OF THE INVENTION

The invention relates to a total body relaxation system having a control for a plurality of vibrating elements, and particularly, to a total body relaxation system having a stress sensing circuit and a display for indicating the level of stress in a subject.

Scientific research has shown that a significant positive effect on stress reduction can help promote a holistic health and lifestyle. Reducing overall stress can help generate healing energy, and prevent premature aging and deterioration of the body's normal psychological balance. Stress reduction can be accomplished through many techniques including muscle relaxation (e.g., through massage) and auditory healing (e.g., listening to various rhythmic sound waves to promote a relaxed state).

One prior art massage apparatus is found in U.S. Pat. No. 4,173,217 to Johnston. The massage apparatus has a pair of electrodes and a massage device. Each electrode is adapted to attach to a finger of the subject being treated, and the massage device is attached to the specific part of the body which appears to be in need of treatment. As the massage is being applied to a particular muscle, the skin resistance of the subject is sensed across the electrodes to provide an audio/visual response that is related to stress in the subject.

SUMMARY OF THE INVENTION

When using the massage apparatus of the Johnston Patent, only a small part of the body (i.e., an individual muscle) is being relieved of stress. Accordingly, the amount of stress reduction measured is only for the effect of the massage on a particular muscle or a particular area of the body. It would be more beneficial for the subject receiving the stress relaxation to have total body stress relief as well as a system for measurement and display of total body stress.

The total body relaxation system of the invention creates a rhythmic audible and vibrating stimulus that is conveyed to the brain through tactile and auditory nerves. A subject feels rhythmic vibrating waves being generated from the total body relaxation system while hearing the rhythm of those waves. The rhythmic waves are smooth from one vibration to the next causing the subject to relax. Thus, the combination of a rhythmic tactile and auditory stimulus reduces overall stress in the user of the unit.

Accordingly, the total body relaxation system of the invention provides a plurality of massage wands, controlled by a control circuit. The massage wands provide whole body relaxation through tactile and auditory rhythms. This is accomplished by the massage wands providing rhythmic vibration and audible sound. The control circuit is connected to the massage wands to provide a control signal to energize the massage wands. Additionally, the control circuit and the massage wands are electrically connected to an AC/DC transformer through a junction box.

The control circuit includes a stress sensing circuit for measuring total body stress and a display for showing a visual indication of the total relative body stress. The total body stress measurement of a subject is linked to the impedance of an element of the subject's body (e.g. a finger). As the subject's whole body is being relaxed, there is a relative change in the impedance of the element, and thus, in the total body stress measurement. Based on the measurement of total body stress, the operation of the total body relaxation system can be adjusted accordingly. For example, the subject can increase or decrease the frequency of the tactile and auditory rhythms, increase or decrease the intensity of tactile and auditory rhythms, adjust the wave shape of the rhythmic waves, or adjust the overlap of the rhythmic waves.

The control circuit is surrounded by a hand-held housing. Additionally, the control circuit includes a pair of metal contacts external to the housing. That is, the contacts are supported by the housing and extend through the housing sidewall. The metal contacts are connected to the control circuit so that the control circuit measures the impedance of an element connected across the metal contacts. For example, the element may be a finger of the subject being relaxed. The visual display includes a series of light emitting diodes to provide a visual indication of total body stress. In one embodiment, the series of diodes includes diodes of different colors.

The control circuit further includes a microprocessor for measuring the impedance of the element and generating the control signal for the display element to provide a visual indication of total body stress. Depending on the variation of the impedance across the metal contacts of the control circuit, the control circuit will energize the light emitting diodes to provide a visual total body stress measurement. In one embodiment, the relationship between the measured impedance and the resulting control signal for energizing the light emitting diodes is a non-linear, logarithmic relationship.

It is an advantage of this invention to provide a total body relaxation through rhythmic audible and vibrating stimulus. Furthermore, it is an advantage of this invention to provide a total body stress measurement. Based on this measurement, the invention can adjust the rhythmic audible and vibrating stimulus accordingly.

It is another advantage of the invention to adjust the vibration of vibrating elements based on the total body stress. The vibrating elements can be adjusted accordingly in intensity of vibration and frequency of vibration. Additionally, the vibrating elements can be sequentially alternated in speed.

Other features and advantages of the invention are set forth in the following in the following detailed description, drawings and claims.

BRIEF DESCRIPTION OF THE DRAWINGS

FIG. 4 is an electrical schematic of another portion of the control circuit of the total body relaxation system.

Figure 1:
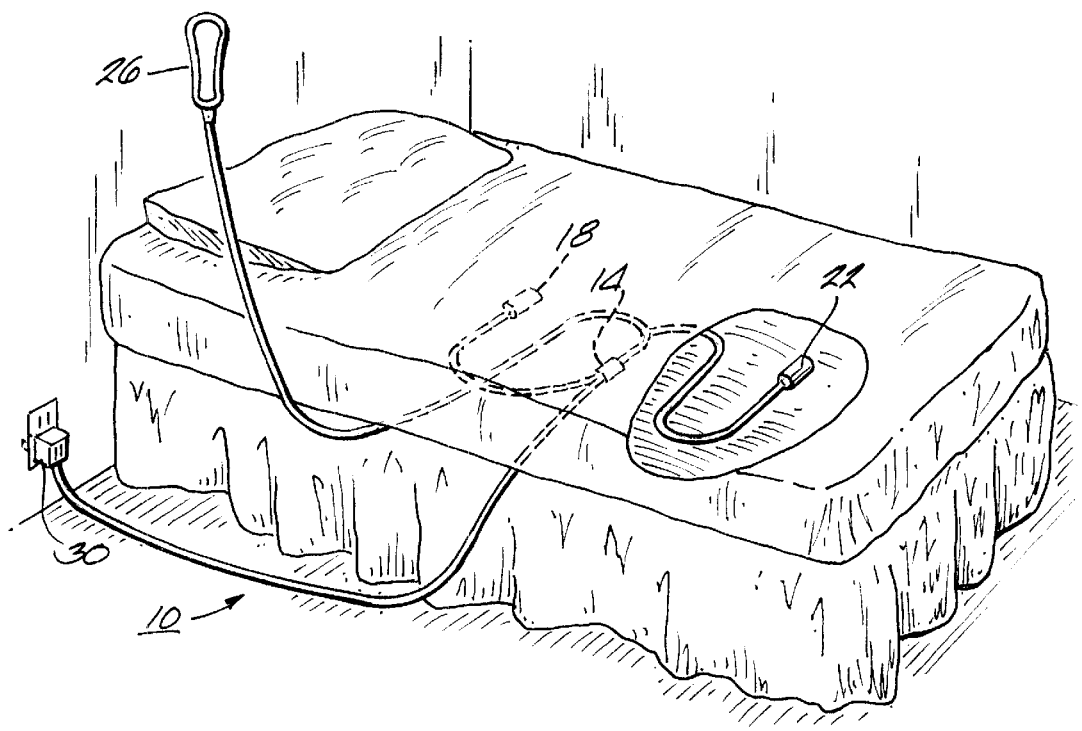
FIG. 1 is a perspective view of a total body relaxation system embodying the invention.

Before one embodiment of the invention is explained in full detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Shown in FIG. 1 of the drawings is a total body relaxation system 10 embodying the invention. The total body relaxation system 10 includes a junction box 14, a plurality of vibrating elements 18 and 22, a hand-held control 26 connected to the vibrating elements 18 and 22 at the junction box 14, and an alternating current-to-direct current (AC/DC) transformer 30 connected to the junction box 14 to provide power to the total body relaxation system 10. The total body relaxation system 10 may be used in a variety of environments including beneath a mattress of a bed as shown in FIG. 1, or as shown in application Ser. No. 09/098,241, Portable Vibrator For Use With Furniture, which is incorporated herein by reference.

The junction box 14 provides an electrical connection between the AC/DC transformer 30 and the hand-held control 26, between the AC/DC transformer 30 and the plurality of vibrating elements 18 and 22, and between the plurality of vibrating elements 18 and 22 and the hand-held control 26. The junction box 14 contains electrical receptacles (not shown) for receiving electrical plugs (not shown) connecting the plurality of vibrating elements 18 and 22, the hand-held control 26, and the AC/DC transformer 30.

The AC/DC transformer 30 is a 12-volt transformer. The transformer plugs into any conventional 120-volt electrical outlet and provides a direct electrical current (DC) to the plurality of vibrating elements 18 and 22 and the hand-held control 26.

The vibrating elements 18 and 22 are identical, and accordingly, only the element 18 will be described in detail. The vibrating element 18 includes a housing and a vibrating motor (not shown) mounted in the housing. The vibrating element 18 provides muscle relaxation through vibration and auditory healing through the generation of rhythmic sound waves audible to the user of the total body relaxation system. It should be understood that while there are two vibrating elements 18 and 22 in the total body relaxation system 10 shown in the diagrams, the number of vibrating elements 18 and 22 can vary. The vibrating elements 18 and 22 can be placed in-between a mattress and a box spring of a bed, as shown in FIG. 1, or can be mounted in any other piece of furniture. The generation of rhythmic vibration and sound waves can be adjusted in intensity by varying the supply of electrical energy to the vibrating elements 18 and 22. Additionally, the vibration can alternate sequentially or randomly among the vibrating elements 18 and 22. Moreover, the alternating vibrating elements 18 and 22 can overlap in vibration from a minimum overlap to a maximum overlap. That is, as one vibrating element 18 is decreasing in intensity of vibration, the second vibrating element 22 is increasing in intensity of vibration. The time the second vibrating element 22 starts increasing intensity of vibration can vary in reference to the time the first vibrating element 18 starts decreasing intensity of vibration.

Figure 2:
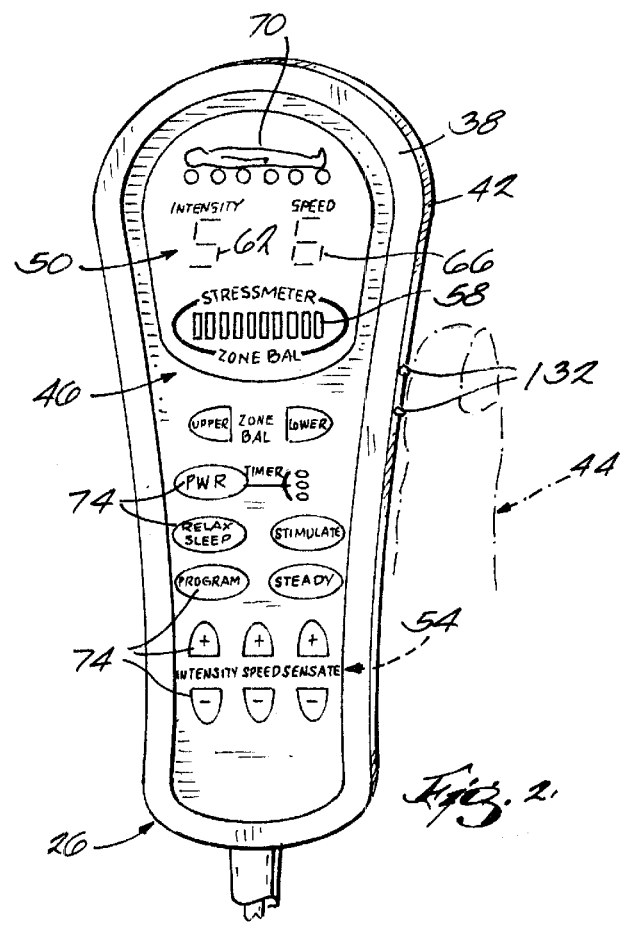
FIG. 2 is a perspective view of the controller of the total body relaxation system.

As shown in FIG. 2, the hand-held control 26 includes a hand-held housing 38 having a continuous sidewall 42 and a front panel 46 supported by the sidewall 42. The front panel 46 includes a visual display area 50 and a subject-entry area 54. The visual display area includes a display element for providing a visual indication of total body stress 58, a display element for providing a visual indication of the intensity of vibration of the vibrating elements 62, a display element for providing a visual indication of the speed of alternation of the vibrating elements 66, and a display element for providing a visual indication of the locations where a subject will feel a vibrating sensation 70. It should be understood that other display elements can be added, as required or desired, for providing a visual indication of other functions of the total body relaxation system 10.

The visual indicator of total body stress 58 includes a series of light emitting diodes (LEDs) which can be of various colors. For example, green, yellow and red LEDs can be used with green designating a low total body stress, yellow designating a neutral total body stress, and red designating a high total body stress. The visual indicators for the intensity of vibration 62 and the speed of alternation of the vibrating elements 66 include seven LEDs to create a zero-to-nine digital number. The visual indicator for the location of the vibrating sensation 70 includes a series of LEDs which can be of various colors.

The subject-entry area includes a plurality of entry buttons 74 that may be pressed by a subject (not shown). The entry buttons 74 allow the subject to control the total body relaxation system 10. For example, the subject can press entry buttons 74 to turn the power of the system 10 on and off; increase or decrease intensity of vibration of the vibrating elements 18 and 22; increase or decrease speed of alternation of the vibrating elements 18 and 22; increase or decrease vibration overlap between the vibrating elements 18 and 22; turn pre-made vibrating control programs which control the intensity of vibration, speed of alternation and overlapping of vibration of the vibrating elements on and off; or create and recall user-made programs which control the intensity of vibration, speed of alternation, and the amount of vibration overlap of the vibrating elements 18 and 22. It should be understood that other options can be added with corresponding entry buttons for controlling such options. The total body relaxation system 10 includes a control circuit 78 (schematically represented in FIGS. 3 and 4) mounted within the hand-held housing 38. The control circuit 78 includes a microprocessor 82 (FIG. 3), a stress sensing circuit 86 (FIG. 3), a vibrating circuit 90 (FIG. 3), a display circuit 94 (FIG. 4) and a subject-entry circuit 98 (FIG. 4).

The microprocessor 82 includes a programmable read only memory (not shown) containing program logic. The microprocessor 82 receives inputs from the stress sensing 86 and subject-entry 98 circuits through pins 100 and 105–107, respectively. After receiving the inputs, the program logic interprets and processes the inputs. In response to the inputs, the microprocessor 82 provides outputs for controlling the display and vibrating circuits 94 and 90, respectively, through pins 120–129, and 110 and 111, respectively. Additionally, pins 125–129 of the microprocessor 82 provides a zero-walking pattern (discussed below) which controls the display 94 and subject entry 98 circuits.

Figure 3:
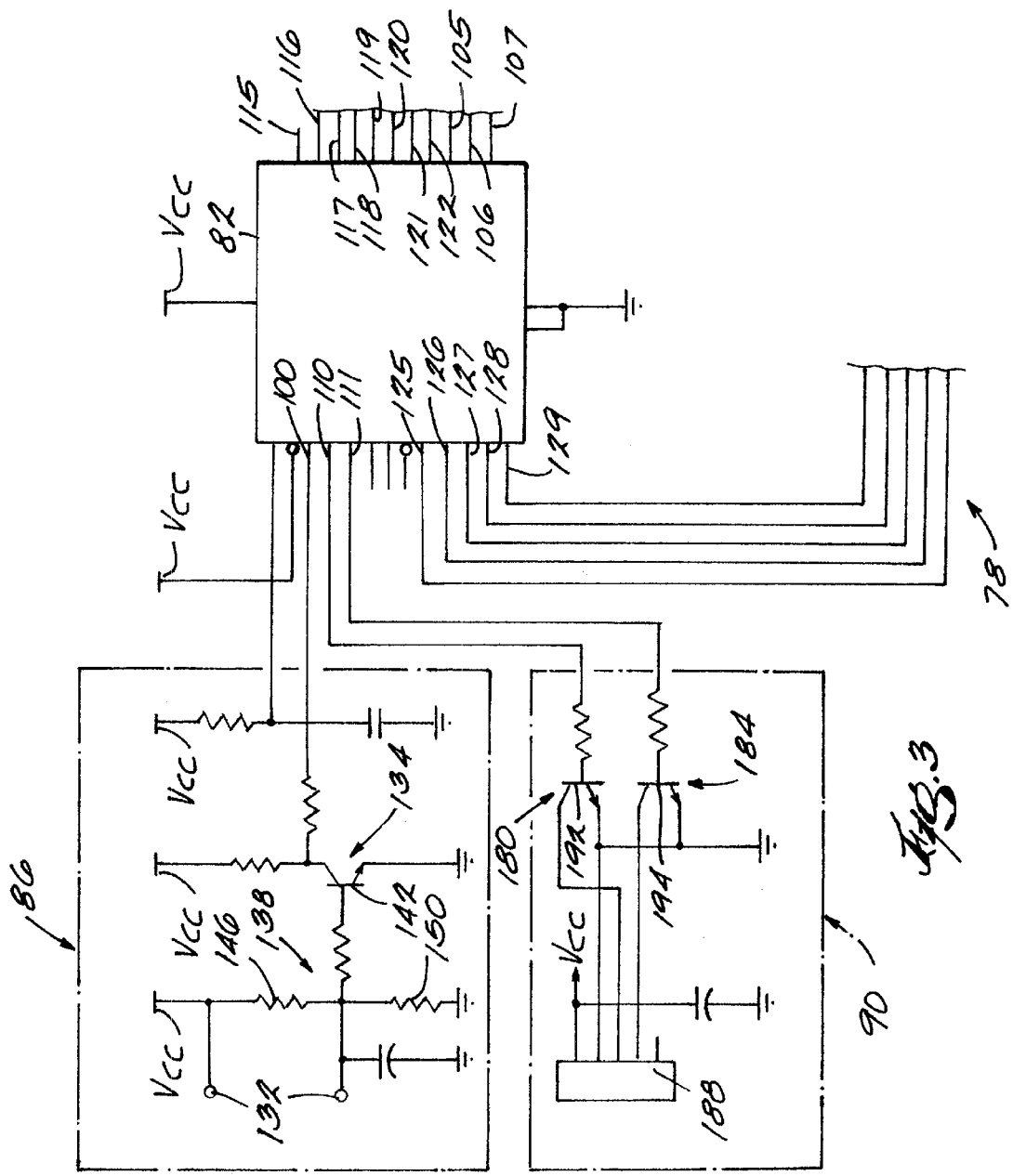
FIG. 3 is an electrical schematic of a portion of the control circuit of the total body relaxation system.

As shown in FIG. 3, the stress sensing circuit 86 includes a pair of metal contacts 132 connected to an amplifier 134 through a voltage divider network 138. The voltage divider network 138 forms the input to transistor 142 which amplifies the voltage between resistors 146 and 150 and provides an output to the microprocessor 82 that is indicative of the impedance of an element connected across the contacts 132 (such as a finger 44 as shown in FIG. 2.) The pair of metal contacts 132 extend through the housing sidewall 42 (FIG. 2).

As shown in FIG. 3, the vibrating circuit 90 includes two switching circuits 180 and 184 and a coupler 188. Each switching circuit 180 and 184 corresponds to one of the vibrating elements 18 and 22 and includes one npn transistor 192 and 194. The coupler 188 is mounted within the junction box 14 (FIG. 1) and couples each switching circuit 180 and 184 with its corresponding vibrating element 18 and 22. If one of the switching circuits 180 or 184 is active, the corresponding vibrator 18 or 22 is on.

The microprocessor 82 generates an electrical stimulus at pins 110 and 111 that causes the switching circuits 180 and 184, respectively, to be active or non-active. If the switching circuits 180 or 184 are active, a current flows through transistors 192 or 194, respectively, from the transistor collector to the transistor emitter. The current entering the transistor collector is the current being applied to the respective vibrating element 18 or 22.

As shown in FIG. 4, the subject-entry circuit 98 consists of a matrix of entry button switches and a plurality of diodes. The matrix of entry button switches corresponds to the plurality of entry buttons 74 (FIG. 2) in the subject entry area 54. The program logic of the microprocessor 82 recognizes which button 74 is being pressed by creating a zero-walking pattern at pins 125–129. That is, a low voltage signal (digital logic of 0) will be generated at one of the pins 125–129 and a high voltage signal (digital logic of 1) will be generated at the remaining four pins. The low voltage signal will sequentially alternate, or "walk", through pins 125–129 creating a zero-walking pattern. The pin that is at the low voltage signal is the "active" circuit. The rate of the zero-walking pattern is preferably 1 khz or faster.

The zero-walking pattern at pins 125–129 which will sequentially activate one array of switches in the matrix of entry button switches. Additionally, the microprocessor 82 creates an internal signal that has a logic of 1 for each input pin 105–107 of the subject-entry circuit. When a subject depresses one of the entry buttons 74, a closed circuit is created causing the internal signal in the microprocessor to go to a logic of zero when the array of entry switches having the depressed entry button is active. Thus, the microprocessor recognizes which entry button is pressed based on what array of entry switches are active and which internal signal has a logic of zero. The zero-walking pattern alternates sufficiently fast enough to register an entry by the subject without the subject having to take any other actions. Furthermore, the diodes within the subject entry circuit 98 prevent any signal from hampering the display circuit 94.

Any suitable relationship between the switches and the microprocessor can be created. As shown in FIG. 4, switch 160 turns the power of the total body relaxation system 10 on or off; switch 161 increases the intensity of vibration; switch 162 decreases the intensity of vibration, switch 163 increases the speed of alternation; switch 164 decreases the speed of alternation; switch 165 increases the amount of wave overlap; switch 166 decreases the amount of wave overlap; switches 167–169 activate pre-made programs controlling vibration intensity, speed of alternation, and amount of vibration overlap of the vibrating elements 18 and 22; switch 170 creates and recalls subject-made programs controlling vibration intensity, speed of alternation, and amount of vibration overlap of the vibrating elements 18 and 22; and switches 171 and 172 manually adjust which vibrating element has a greater intensity of vibration. It should be understood that other buttons can be added to provide input to the microprocessor as functional features of the system are added.

As shown in FIG. 4, the display circuit 94 includes a matrix of LEDs connected to a plurality of pnp transistors 196 and a plurality of npn transistors 200. Each pnp transistor 196 is commonly connected to the supply voltage Vcc at the respective transistor emitter and to a resistor 198 connected to each transistor base. Each npn transistor 200 is commonly connected to a resistor 202 connected to the transistor base and a resistor 204 connected to the transistor collector. As stated above with respect to the user entry circuit, a walking zero pattern is generated at pins 125–129. The walking-zero pattern activates one of the pnp transistors allowing current to flow from the Vcc through the activated pnp switching circuit allowing an array of LEDs to possibly activate. The microprocessor 82 generates a bit pattern at pins 115–122 which will activate certain npn transistors. For example, a bit pattern of 10000000 will allow current to flow through the uppermost npn transistor 200. None of the other npn transistors will be active with a bit pattern of 10000000. Accordingly, depending on which array of LEDs is active and the bit pattern generated at pins 115–122, the LED matrix of the display circuit 94 can be controlled. The rate of the walking-zero pattern is preferably 1 khz or faster, which is sufficiently fast enough that all of the appropriate LEDs appear to be "on" to the subject.

In operation, the subject controls the total body relaxation system 10 by pressing the plurality of entry buttons 74 on the subject-entry area 54. The microprocessor 82 recognizes the pressing of the entry buttons 74 and interprets the action in its program logic. Furthermore, the microprocessor 82 provides an output to the visual display area 50 or the plurality of vibrating elements 18 and 22 based on the interpreted action. Each of these steps the will be described in detail below.

A subject can control the activation and deactivation of the total-body relaxation system 10 by pressing the power button in the subject-entry area 54. The subject will press the button creating a closed circuit that will provide an input to the program logic. The program logic will then turn the system 10 on or off.

Once power has been supplied, the subject can perform a total body stress measurement. The subject engages an element of his body (e.g. a finger 44) with the pair of metal contacts 132. Depending on the impedance of the finger 44, the amplified voltage entering pin 100 is generated. The voltage is indicative of the impedance of the finger 44. It should be noted that the impedance of the finger 44 varies with the moisture content of the skin around the finger 44, and the moisture content varies with the total body stress experienced by the subject.

Stated differently, the amount of stress one is experiencing is directly related to the impedance of the subject's finger 44. Since the vibrating elements 18 and 22 provide total body stress relaxation through muscle relaxation and auditory healing, the impedance measurement will be a total body stress measurement. As the subject is being relaxed, the impedance of the finger 44 will vary resulting in a varying total body stress measurement.

The program logic will convert the input voltage to a total body stress measurement. Once a total body stress measurement is calculated, the microprocessor will activate the appropriate LEDs in the display element for providing a visual indication of total body stress 58. The control of the LEDs is accomplished by the microprocessor 82 providing electrical stimulus to the npn and pnp transistors as discussed above. Based on the total body stress measurement, the microprocessor will activate stress LEDs 210–219 providing a visual indication of total body stress.

For example, a low total body stress may result in only the one LED 210 activating, while a high total body stress may result in all ten LEDs 210–219 activating. Additionally, various color LEDs may be used. For example, LEDs 210–212 are green, representing a low total body stress measurement; LEDs 217–219 are red, representing a high total body stress measurement; and LEDs 213–216 are yellow, representing a neutral total body stress measurement. Moreover, various mathematical relationships between the impedance of the element and the activation of the stress LEDs 210–219 may be used. For example, the mathematical relationship may be linear or nonlinear. In the preferred embodiment, the mathematical relationship is a non-linear, logarithmic relationship. That is, a resistance greater than 76 MΩ energizes zero LEDs, a resistance between 40 MΩ and 76 MΩ energizes LED 210, a resistance between 20 MΩ and 40 MΩ energizes LEDs 210 and 211, a resistance between 12 MΩ and 20 MΩ energizes LEDs 210–212, a resistance between 8.0 MΩ and 12 MΩ energizes LEDs 210–213, a resistance between 5.4 MΩ and 8.0 MΩ energizes LEDs 210–214, a resistance between 3.7 MΩ and 5.4 MΩ energizes LEDs 210–215, a resistance between 3.0 MΩ and 3.7 MΩ energizes LEDs 210–216, a resistance between 2.2 MΩ and 3.0 MΩ energizes LEDs 210–217, a resistance between 1.7 MΩ and 2.2 MΩ energizes LEDs 210–218, and a resistance less than 1.7 MΩ energizes LEDs 210–219. The voltage range entering pin 100 is 0 to 5 volts. Furthermore, the subject can take repeated measurements of total body stress throughout the treatment as desired.

Other LEDs can be used to provide the user with information. Other information provided to the user may include, but is not limited to: displaying a digital number representing the intensity of vibration of the plurality of vibrating elements (LEDs 233–239) displaying a digital number representing the speed of alternation between the vibrating elements (LEDs 241–247), and displaying the locations of the vibrating sensation (LEDs 225–230). Furthermore, each button of the plurality of entry buttons 74 may have an LED which enlightens the entry button (LEDs 220–224, 231, 232 and 240).

The subject can vary the intensity and alternation of the vibrating elements 18 and 22 at any time. Moreover, the microprocessor 82 can contain pre-made programs that will control the vibrating elements. For example, based upon an initial indication of total body stress, the subject can select an intensity vibration level of five. If the vibrating level is at its lowest intensity, the display element for intensity of vibration 62 will indicate a level of one. The subject can increase the amount of vibration by pressing the increase intensity entry button on the subject-entry area 98. This will result in a closed circuit that will register with the program logic of the microprocessor 82 as described above. The microprocessor 82 will increase the electrical stimulus to the vibrating elements 18 and 22 as the increase intensity button is being pressed. This can by done by increasing the frequency of switching in the vibrating circuit 90 as described in application Ser. No. 08/922,903, Control For Vibratory Motor, which is incorporated herein by reference. Additionally, the corresponding intensity LEDs 233–239 will activate as the amount of vibration is increased. The subject holds the intensity entry button until the number representing the intensity of vibration displays a five. Although this process was described for changing the intensity of vibration, other features, including changing the speed of alternation and changing the amount of alternation overlap can be done similarly.

Moreover, while the embodiment described above requires the subject to manually change the operating state in response to the relative stress level observed by the subject, alternative embodiments (not shown) may automatically adjust the operating state in response to the measured impedance.

Various features and advantages of the invention are set forth in the following claims.

What is claimed is:

1. A total body relaxation system comprising:
    a plurality of vibrating elements; and
    a control circuit connected to the vibrating elements to provide an electrical stimulus to energize the vibrating elements, the control circuit including a stress sensing circuit for sensing relative total body stress and a display element for providing a visual indication of total body stress.

2. A total body relaxation system as set forth in claim 1, further comprising a hand-held control including a housing and wherein the control circuit is mounted in the housing.

3. A total body relaxation system as set forth in claim 2, wherein the control circuit further includes a pair of metal contacts external to the housing, the metal contacts being connected to the control circuit so that the control circuit measures impedance of an element connected across the metal contacts.

4. A total body relaxation system as set forth in claim 1, wherein the display element is a series of light emitting diodes.

5. A total body relaxation system as set forth in claim 4, wherein the series of light emitting diodes includes light emitting diodes of differing colors.

6. A total body relaxation system as set forth in claim 1, wherein the control circuit further includes a microprocessor for measuring the impedance of a subject and generating a control signal for the display element to provide a visual indication of total body stress.

7. A total body relaxation system as set forth in claim 6 wherein the control signal has a mathematical relationship with the measured impedance.

8. A total body relaxation system as set forth in claim 7 wherein the mathematical relationship between the control signal and the measured impedance is non-linear.

9. A total body relaxation system as set forth in claim 7 where the mathematical relationship between the control signal and the measured impedance is logarithmic.

10. A total body relaxation system as set forth in claim 6, further comprising means for controlling the electrical stimulus to the plurality of vibrating elements based on the measured impedance of total body stress.

11. A total body relaxation system as set forth in claim 1, wherein the vibration of the vibrating elements can be varied in intensity.

12. A total body relaxation system as set forth in claim 1, wherein the vibration of the vibrating elements sequentially alternates between the vibrating elements.

13. A total body relaxation system as set forth in claim 12, wherein the sequentially alternating vibrating elements can vary in speed of sequential alternation.

14. A total body relaxation system as set forth in claim 13, wherein the vibrating elements generate a rhythmic audible sound to promote relative stress reduction.

15. A method of providing a total body relaxation stimulus to a subject, the method comprising the acts of:
    providing a plurality of vibrating elements;
    generating an electrical stimulus to energize the vibrating elements; and
    measuring the impedance across a portion of the subject to provide an indication of total body stress in the subject.

16. The method as set forth in claim 15, further comprising the acts of providing a display element, and energizing the display element to provide a visual indication of total body stress.

17. The method as set forth in claim 15, wherein the generating of the electrical stimulus is dependent on the measurement of the impedance of the subject.

18. The method as set forth in claim 16, wherein the energizing of the display element is mathematically dependent on the measured impedance.

19. The method as set forth in claim 18, wherein the mathematical dependency between the display element and the measured impedance is non-linear.

20. The method as set forth in claim 18, wherein the mathematical dependency between the display element and the measured impedance is logarithmic.

21. The method as set forth in claim 15, wherein the electrical stimulus can be varied in intensity.

22. The method as set forth in claim 15, wherein the generating of the electrical stimulus further comprises the acts of sequentially alternating the vibrating elements.

23. The method as set forth in claim 22, wherein the sequentially alternating vibrating elements can vary in speed of sequential alternation.

24. A total body relaxation system comprising:
   a plurality of vibrating elements;
   a hand-held control including a housing; and
   a control circuit mounted to the housing and connected to the vibrating elements to provide an electrical stimulus to energize the vibrating elements, the control circuit including:
      a stress sensing circuit for sensing total body stress,
      a pair of metal contacts external to the housing, the metal contacts being connected to the control circuit so that the control circuit measures impedance of an element connected across the metal contacts, and
      a display element having a series of light emitting diodes for providing a visual indication of total body stress.

25. A total body relaxation system as set forth in claim 24, wherein the series of light emitting diodes includes light emitting diodes of differing colors.

26. A total body relaxation system as set forth in claim 24, wherein the control circuit further includes a microprocessor for measuring the impedance of a subject and generating a control signal for the display element to provide a visual indicator of total body stress.

27. A total body relaxation system as set forth in claim 24, wherein the vibration of the vibrating elements can be varied in intensity.

28. A total body relaxation system as set forth in claim 24, wherein the vibration of the vibrating elements sequentially alternates between the vibrating elements.

29. A total body relaxation system as set forth in claim 28, wherein the sequentially alternating vibrating elements can vary in speed of sequential alternation.

30. A total body relaxation system as set forth in claim 26, wherein the control signal has a mathematical relationship with the measured impedance.

31. A total body relaxation system as set forth in claim 30, wherein the mathematical relationship between the control signal and the measured impedance is nonlinear.

32. A total body relaxation system as set forth in claim 30, wherein the mathematical relationship between the control signal and the measured impedance is logarithmic.

33. A total body relaxation system as set forth in claim 24, further comprising means for controlling the electrical stimulus to the vibrating elements based on a reading of the display element.

34. A method of providing a total body relaxation stimulus to a subject, the method comprising the acts of:
   providing a plurality of vibrating elements;
   providing a display element;
   generating a electrical stimulus to energize the vibrating elements;
   measuring the impedance across a portion of the subject to provide an indication of total body stress in the subject; and
   energizing the display element to provide a visual indication of total body stress.

35. The method as set forth in claim 34, wherein the energizing of the display element is mathematically dependent on the measured impedance.

36. The method as set forth in claim 35, wherein the mathematical dependency between the display element and the measured impedance is non-linear.

37. The method as set forth in claim 35, wherein the mathematical dependency between the display element and the measured impedance is logarithmic.

38. The method as set forth in claim 34, wherein the electrical stimulus can be varied in intensity.

39. The method as set forth in claim 34, wherein the generating of the electrical stimulus further comprises the acts of sequentially alternating the vibrating elements.

40. The method as set forth in claim 39, wherein the sequentially alternating vibrating elements can vary in speed of sequential alternation.

* * * * *